(12) United States Patent
Harris

(10) Patent No.: US 6,432,397 B1
(45) Date of Patent: Aug. 13, 2002

(54) DELIVERY OF POLY(ETHYLENE GLYCOL)-MODIFIED MOLECULES FROM DEGRADABLE HYDROGELS

(75) Inventor: J. Milton Harris, Huntsville, AL (US)

(73) Assignee: Debio Recherche Pharmaceutique S. A., Martigny (CH)

( * ) Notice: Subject to any disclaimer, the term of this patent is extended or adjusted under 35 U.S.C. 154(b) by 0 days.

(21) Appl. No.: 09/426,289

(22) Filed: Oct. 25, 1999

Related U.S. Application Data

(62) Division of application No. 08/964,972, filed on Nov. 5, 1997, now Pat. No. 6,258,351.
(60) Provisional application No. 60/030,453, filed on Nov. 6, 1996.

(51) Int. Cl.[7] .................. A61K 31/77; C08G 65/48; C08G 81/00
(52) U.S. Cl. ............... 424/78.3; 525/54.1; 525/403; 530/816
(58) Field of Search .................. 424/486, 487, 424/78.3, 78.27; 514/772.4, 772.6, 772.7, 944; 525/54.1, 403; 530/816, 815

(56) References Cited

U.S. PATENT DOCUMENTS

| | | |
|---|---|---|
| 3,149,006 A | 9/1964 | Abel et al. |
| 3,419,006 A | 12/1968 | King |
| 3,963,805 A | 6/1976 | Chu |
| 4,179,337 A | 12/1979 | Davis et al. |
| 4,424,311 A | 1/1984 | Nagaoka et al. |
| 4,670,417 A | 6/1987 | Iwasaki et al. |
| 4,894,238 A | 1/1990 | Embry et al. |
| 5,567,422 A | 10/1996 | Greenwald |
| 5,618,528 A | 4/1997 | Cooper et al. |
| 5,730,968 A | 3/1998 | Butterfield et al. |
| 5,874,500 A | 2/1999 | Rhee et al. |

FOREIGN PATENT DOCUMENTS

| | | |
|---|---|---|
| EP | 0 473 268 | 3/1992 |
| EP | 0 841 360 | 5/1993 |
| WO | WO92/00748 | 1/1992 |
| WO | WO93/24476 | 12/1993 |
| WO | WO96/21469 | 7/1996 |

OTHER PUBLICATIONS

J.M. Harris, Ed., "Biomedical and Biotechnical Applications of Poly(Ethylene Glycol) Chemistry", Plenum, New York, 1992.

Greenwald et al., "Highly Water Soluble Taxol Derivatives: 7–Polyethylene Glycol Carbamates and Carbonates", *J. Org. Chem.*, vol. 60, No. 2, pp. 331–336, 1995.

Sawhney et al., "Biorodible Hydrogels Based on Photopolymerized Poly(Ethylene Glycol)–co–poly(α–hydroxy acid) Diacrylate Macromers", *Macromolecules*, vol. 26, No. 4, pp. 581–587 (1993).

Gayet et al., "High Water Content BSA–PEG Hydrogel for Controlled Release Device: Evaluation of the Drug Release Properties", *Journal of Controlled Release 38*, pp. 177–184 (1996).

Martinez A et al: "Branched Poly(Ethylene Glycol) Linkers", *Macromolecular Chemistry And Physics*, vol. 198, No. 8, Aug. 1997, pp. 2489–2498.

Jeong B et al: "Biodegradable Block Copolymers As Injectable Drug—Delivery Systems", *Nature*, vol. 388, No. 6645, Aug. 28, 1997, pp. 860–862.

Zalipsky S: "Functionalized Poly(Ethylene Glycol) For Preparation Of Biologically Relevant Conjugates", *Bioconjugate Chemistry*. vol. 6, NO. 2, 1995, pp. 150–165.

Pitt C G et al: "Manipulation Of The Rate Of Hydrolysis Of Polymer–Drug Conjugates: The Secondary Structure Of The Polymer", *Journal Of Controlled Release*, vol. 39, No. 2, May 1996, pp. 221–229.

*Primary Examiner*—Edward J. Webman
(74) *Attorney, Agent, or Firm*—Alston & Bird LLP

(57) ABSTRACT

A degradable PEG hydrogel is described that, upon hydrolysis, releases conjugates of substantially non-peptidic polymers and biologically active molecules. For example, PEG and protein conjugates can be released in vivo from the hydrogels for therapeutic application.

40 Claims, 1 Drawing Sheet

DELIVERY OF POLY(ETHYLENE GLYCOL)-MODIFIED MOLECULES FROM DEGRADABLE HYDROGELS

CROSS REFERENCE TO RELATED APPLICATION

This application is a divisional of Ser. No. 08/964,972 filed Nov. 5, 1997 now U.S. Pat. No. 6,258,351 and is related to commonly owned copending Provisional Application Serial No. 60/030,453, filed Nov. 6, 1996, and claims the benefit of its earlier filing date under 35 U.S.C. 119(e).

FIELD OF THE INVENTION

This invention relates to crosslinked hydrogel networks that include the hydrophilic polymer poly(ethylene glycol).

BACKGROUND OF THE INVENTION

Chemical attachment of the hydrophilic polymer poly(ethylene glycol )(PEG), also known as polyethylene oxide) (PEO), to molecules and surfaces is of great utility in biotechnology. In its most common form, PEG is a linear polymer terminated at each end with hydroxyl groups:

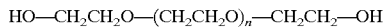

This polymer can be represented in brief form as HO—PEG—OH where it is understood that the —PEG— symbol represents the following structural unit:

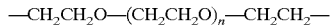

In typical form, n ranges from approximately 10 to approximately 2000.

PEG is commonly used as methoxy-PEG—OH, or mPEG in brief, in which one terminus is the relatively inert methoxy group, while the other terminus is a hydroxyl group that is subject to ready chemical modification.

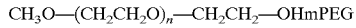

PEG is also commonly used in branched forms that can be prepared by addition of ethylene oxide to various polyols, such as glycerol, pentaerythritol and sorbitol. For example, the four-arm, branched PEG prepared from pentaerythritol is shown below;

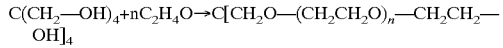

The branched PEGs can be represented in general form as R(—PEG—OH)$_n$ in which R represents the central "core" molecule, such as glycerol or pentaerythritol, and n represents the number of arms.

PEG is a much used polymer having the properties of solubility in water and in many organic solvents, lack of toxicity,land lack of immunogenicity. One use of PEG is to covalently attach the polymer to insoluble molecules to make the resulting PEG-molecule "conjugate" soluble. For example, Greenwald, Pendri and Bolikal in *J. Org. Chem.*, 60, 331–336 (1995) have shown that the water-insoluble drug taxol, when coupled to PEG, becomes water soluble.

Davis et al. U.S. Pat. No. 4,179,337 describes proteins coupled to PEG and having enhanced blood circulation lifetime because of reduced rate of kidney clearance and reduced immunogenicity. The lack of toxicity of the polymer and its rapid clearance from the body are advantageous features for pharmaceutical applications. These applications and many leading references are described in the book by Harris (J. M. Harris, Ed., "Biomedical and Biotechnical Applications of Polyethylene Glycol Chemistry," Plenum, New York, 1992).

To couple PEG to a molecule such as a protein it is necessary to use an "activated derivative" of the PEG having a functional group at the terminus suitable for reacting with some group on the surface or on the protein (such as an amino group). Among the many useful activated derivatives of PEG is the succinimidyl "active ester" of carboxymethylated PEG as disclosed by K. Iwasaki and Y. Iwashita in U. S. Pat. No. 4,670,417. This chemistry is illustrated with the active ester reacting with amino groups of a protein (the succinimidyl group is represented as NHS and the protein is represented as PRO-NH$_2$):

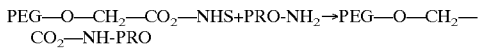

Succinimidyl "active esters", such as PEG—O—CH$_2$—CO$_2$—NHS, are commonly used forms of activated carboxylic acids, and they are prepared by reacting carboxylic acids with N-hydroxylsuccinimide.

Problems have arisen in the art. Some of the functional groups that have been used to activate PEG can result in toxic or otherwise undesirable residues when used for in vivo drug delivery. Some of the linkages that have been devised to attach functional groups to PEG can result in an undesirable immune response. Some of the functional groups do not have sufficient or otherwise appropriate selectivity for reacting with particular groups on proteins and can tend to deactivate the proteins.

PEG hydrogels, which are water-swollen gels, have been used for wound covering and drug delivery. PEG hydrogels are prepared by incorporating the soluble, hydrophilic polymer into a chemically crosslinked network or matrix so that addition of water produces an insoluble, swollen gel. Substances useful as drugs typically are not covalently attached to the PEG hydrogel for in vivo delivery. Instead, the substances are trapped within the crosslinked matrix and pass through the interstices in the matrix. The insoluble matrix can remain in the body indefinitely and control of the release of the drug can be somewhat imprecise.

One approach to preparation of these hydrogels is described in Embrey and Graham's U.S. Pat. No. 4,894,238, in which the ends of the linear polymer are connected by various strong, nondegradable chemical linkages. For example, linear PEG can be incorporated into a crosslinked network by reacting with a triol and a diisocyanate to form hydrolytically-stable ("nondegradable") urethane linkages.

A related approach for preparation of nondegradable PEG hydrogels Las been demonstrated by Gayet and Fortier in *J. Controlled Release*, 38, 177–184 (1996) in which linear PEG was activated as the p-nitrophenylcarbonate and crosslinked by reaction with a protein, bovine serum albumin. The linkages formed are hydrolytically-stable urethane groups.

N. S. Chu U.S. Pat. No. 3,963,805 describes nondegradable PEG networks have been prepared by random entanglement of PEG chains with other polymers formed by use of free radical initiators mixed with multifunctional monomers. P. A. King U.S. Pat. No. 3,419,006 describes the preparation of nondegradable PEG hydrogels by radiation-induced crosslinking of high molecular weight PEG.

Nagaoka et al. U.S. Pat. No. 4,424,311 describes PEG hydrogels prepared by copolymerization of PEG methacrylate with other comonomers such as methyl methacrylate. This vinyl polymerization will produce a polyethylene backbone with PEG attached. The methyl methacrylate comonomer is added to give the gel additional physical strength Sawhney, Pathak and Hubbell in *Macromolecules*, 26, 581 (1993) describe the preparation of block copolymers of polyglycolide or polylactide and PEG that are terminated with acrylate groups, as shown below:

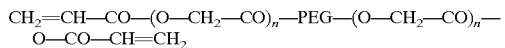

In the above formula, the glycolide blocks are the —O—CH$_2$—CO— units; addition of a methyl group to the methylene gives a lactide block; n can be multiples of 2. Vinyl polymerization of the acrylate groups produces an insoluble, crosslinked gel with a polyethylene backbone. The polylactide or polyglycolide segments of the polymer backbone, being ester groups, are susceptible to slow hydrolytic breakdown, with the result that the crosslinked gel undergoes slow degradation and dissolution.

Substantial non-PEG elements are introduced into the hydrogel. Non-PEG elements tend to introduce complexity into the hydrogelland degradation and dissolution of the matrix can result in undesirable or toxic components being released into the blood stream when the hydrogels are used in vivo for drug delivery.

It would be desirable to provide alternative PEG hydrogels that are suitable for drug delivery and that have unique properties that could enhance drug delivery systems.

SUMMARY OF THE INVENTION

The invention provides chemically crosslinked PEG hydrogels for controlled release of conjugates of PEG and various molecules, including, for example, conjugates of PEG and enzyme's, polypeptides, drugs, nucleosides, phospholipids, and other bioactive substances. The invention also provides methods for preparing the hydrogels.

The hydrogels of the invention are formed by reaction of active derivatives of poly(ethylene glycol) with amine groups on the bioactive substance or other molecule and with amine groups on other poly(ethylene glycol) molecules or related similar nonpeptidic polymers that typically do not contain hydrolytically unstable linkages. The polyethylene glycol) molecules that contain weak linkages in their backbones permit hydrolytic degradation of the crosslinks in the polymer matrix and release of the biloactive substance with the other poly(ethylene glycol) or related nonpeptidic polymer attached. Degradation of the gel in vivo releases PEG/molecule conjugates into the blood stream and produces substantially nontoxic polymer fragments that typically are cleared from the body. Variation of the atoms near the hydrolytically unstable linkages can provide precise control of hydrolytic breakdown rate and release of the conjugate.

Examples of hydrolytically unstable linkages in the PEG polymer backbone include carboxylate ester, phosphate ester, acetals, imines, orthoesters, peptides, anhydrides, ketals, and oligonucleotides. These weak links are formed:by reaction of two PEGs having different terminal groups as illustrated below:

In the above illustration, —W— represents the hydrolytically unstable weak link. Z— and Y— represent groups located at the terminus of the PEG molecule that are capable of reacting with each other to form weak links —W—. Examples of pairs of Z and Y groups that react to form hydrolytically unstable linkages W include pairs selected from the group consisting of alcohol, and carboxylic acid reacting to form carboxylate esters, amine and aldehyde reacting to form imines, hydrazide and aldehyde reacting to form hydrozones, alcohol and phosphate reacting to form phosphate ester, aldehyde and alcohol reacting to form acetals, alcohols and formats reacting to form orthoesters, peptides formed by the reaction of PEG amine with PEG-peptide terminated with carboxyl to form a new peptide linkage, peptides formed by the reaction of PEG carboxylic acid with PEG-peptide terminated wit amine to form a new peptide linkage, and oligonucleotides formed by reaction of PEG phosphoramidite with an 5'-hydroxyl-terminated PEG oligonucleotide.

For example, the following pairs of Z and Y groups can be used to form some of the W groups described above:

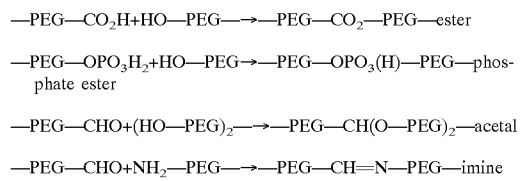

The PEG hydrogels gels are prepared by mixing three ingredients: (1) a PEG with hydrolytically unstable linkages W in the backbone and with reactive groups X at the ends of the chain, (2) a branched PEG or related nonpeptidic polymer with reactive groups Q at the ends of the chain, and (3) a bioactive molecule or other molecule containing reactive groups Q. Reactive groups X are select ed from the group consisting of succinimidyl (NHS), as in —O—(CH$_2$)$_n$—CO$_2$—NHS or —O—CO$_2$—NHS, and related activating groups, including sulfosuccinimidyl, benzotriazole, and p-nitophenyl. Reactive groulps Q typically are amine, —NH$_2$.

A crosslinked network is produced that is held together by hydrolytically unstable groups W and groups T, which are hydrolytically stable. Hydrolysis of the unstable groups W releases the bioactive or other molecule with PEG or a related polymer attached, usually by a covalent linkage., which is hydrolytically stable.

The degree of branching of the polymers can be varied in the hydrogels of this invention to control the physical strength and compressibility of the gels. In general, the greater the degree of branching and the shorter the branches, the greater the strength of the gels, the smaller the pores,land the lower the water content. Strength in this context is defined as resistance to compression or stretching.

The rate of release:e of molecules trapped within the hydrogel matrix is controlled by controlling the hydrolytic breakdown rate of the gel. The hydrolytic breakdown rate oft, the gel can be adjusted by controlling the degree of bonding of the PEGs that form the hydrogel matrix. A multiarm PEG having 10 branches or arms will break down and release drug molecules more slowly than a 3 arm PEG.

The following PEG has been made with two hydrolytically unstable ester linkages in its backbone:

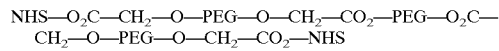

The above PEG is activated at each terminus with an N-hydroxylsuccinimide moiety (NHS) in which the active succinimidyl ester moiety is NHS—CO$_2$— and is reactive with amino groups. A crosslinked network is produced that is held together by stable amide linkages and by hydrolytically unstable ester linkages when the above molecule is coupled with a multiarm PEG amine and with, for example, a protein that contains additional amino groups. The stable amide linkages are formed from reaction of the active NHS ester with amine.

The above example illustrates some of the advantageous features of the invention. First, the crosslinked network degrades, or breaks down because of hydrolysis of the hydrolytically unstable ester linkages (W) in the PEG backbone. Second, when the gel breaks down, it releases PEG and protein conjugates, potentially useful for therapeutic application. Third, subtle variation of the ester linkage provides control over the hydrolytic breakdown rate.

In the above example the ester linkage has the following structure:

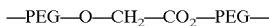

—PEG—O—CH$_2$—CO$_2$—PEG—

This ester group will hydrolyze with a half life of 4 days at pH 7 and 37° C. However, if an ester with the following structure is used, then the half life of hydrolytic degradation of the ester linkages is 43 days at pH 7 and 37° C.

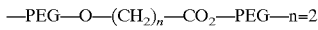

—PEG—O—(CH$_2$)$_n$—CO$_2$—PEG—n=2

Thus, by controlling the identity of the atoms adjacent to the ester linkage it is possible to vary the hydrolytic breakdown rate of the gel. Hence, it is possible to control the rate of release of PEG and protein conjugates bound within the matrix. In general, increasing the n value, which is the number of methylene groups in the above structure, decreases the hydrolysis rate.

Thus, the invention provides, among other things, degradable PEG hydrogels having hydrolytically unstable linkages in which the rate of hydrolysis of the unstable linkages can be controlled for release into the blood stream of conjugates of PEG or related nonpeptidic polymers and proteins or other molecules having some therapeutic effect.

The foregoing and other objects of the invention, and the manner in which the same are accomplished, will be more readily apparent upon consideration of the following detailed description of the invention taken in conjuction with the accompanying drawing, which illustrates an exemplary embodiment.

DETAILED DESCRIPTION

Figure 1:
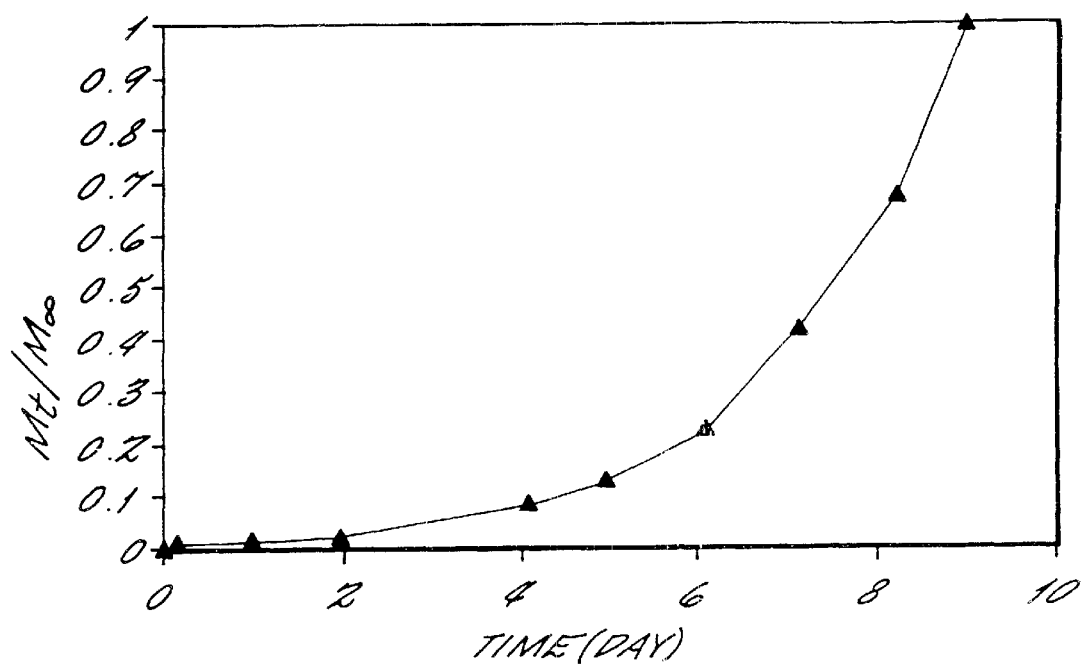
FIG. 1 is a release profile from a PEG hydrogel prepared in accordance with the invention of a model protein (FITC-BSA) covalently linked to PEG.

Hydrogels made from the crosslinked PEG polymeric structures of the invention can be used in drug delivery systems and for wound dressings. Wound dressings could be used internally to provide dressings that degrade within the body over time. The hydrogels of the invention could be usefully applied in drug delivery systems to burns to apply polymer conjugated therapeutic agents to burns. Drug delivery systems can be prepared in which the rate of hydrolysis of the hydrogel is controlled to provide controlled release of drug components.

By "drug" is meant: any substance intended for the diagnosis, cure, mitigation, treatment, or prevention of disease in humans and other animals, or to otherwise enhance physical or mental well being. The invention could be used for delivery of biologically active substances generally that have some activity or function in a living organism or in a substance taken from a living organism.

The terms "group," "functional group," "moiety," "active moiety," "reactive site," and "radical" are all somewhat synonymous in the chemical arts and are used in the art and herein to refer to distinct, definable portions or units of a molecule and to units that perform some function or activity and are reactive with other molecules or portions of molecules.

The term "linkage" is used to refer to groups that normally are formed as the result of a chemical reaction and typically are covalent linkages. Hydrolytically stable linkages means that the linkages are stable in water and do not react with water at useful pHs for an extended period of time, potentially indefinitely. Hydrolytically unstable linkages are those that react with water, typically causing degradation of a hydrogel and release of substances trapped within the matrix. The linkage is said to be subject to hydrolysis and to be hydrolyzable. The time it takes to degrade the crosslinked polymeric structure is referred to as the rate of hydrolysis and is usually measured in terms of its half life.

The skilled artisan should recognize that when reference is made to a Z moiety reacting with a Y moiety, that additional reagents or steps may be employed according to commonly accepted chemical procedures and standards to achieve the desired linkage Was the case may be. There are many possible routes, too numerous to mention here, that could be taken and that should be readily apparent to the skilled artisan. For example, one of skill in the art can be expected to understand that when an alcohol and a carboxylic acid are reacted, the acid typically is converted to another form, the acid chloride, prior to reaction with alcohol. Several examples are demonstrated in the Examples below.

It should also be recognized that related branched non-peptidic polymers that do not have hydrolytically unstable linkages can be used instead of the branched PEG polymer as an ingredient in the preparation of the hydrogels of the invention. These other branched polymers include poly (vinyl alcohol) ("PVA"); other poly(alkylen oxides) such as poly(propylene glycol) ("PPG") and the like; and poly (oxyethylated polyols) such as poly(oxyethylated glycerol), poly(oxyethylated sorbitol), and poly(oxyethylated glucose), and the like. The polymers can be homopolymers or random or block copolymers and terpolymers based on the monomers of the above polymers, straight chain or branched, or substituted or unsubstituted similar to mPEG and other capped, monofunctional PEGs having al single active site available for attachment to la linker.

Specific examples of suitable additional polymers include poly(oxazoline), poly(acryloylmorpholine) ("PAcM") as described in published Italian Pat. Application MI-92-A-0002616 filed Nov. 17, 1992, and poly(vinylpyrrolidone) ("PVP"). PVP and poly(oxazoline) are well known polymers in the art and their preparation and use in the syntheses described with branched PEG should be readily apparent to the skilled artisan.

The following examples illustrate preparation of PEGs having hydrolytically unstable linkages in the polymer backbone and their use in preparing degradable hydrogels for the release of PEG and biomolecule conjugates. PEGs having hydrolytically unstable linkages and their preparation are also described in a copending patent application U.S. Ser. No. 08/928,049 entitled Degradable Poly(ethylene glycol) Hydrogels With Controlled Half-life and Precursors Therefor, which was filed on Sep. 12, 1997 and claims priority from Provisional Application Serial No. 60/026,066, which was filed on Sep. 13, 1996, the contents of which relating to the preparation of PEGs having hydrolytically unstable linkages in the polymer backbone are incorporated by reference in their entirety.

EXAMPLES

Example 1

Synthesis of PEG Derivatives Having Hydrolytically Unstable Backbone Linkages and Terminal NHS Active Carbonates (NHS—OOCO—PEG—W—PEG—OCOO—NHS)

In a 100 ml round-bottom flask, benzyloxy-PEG carboxymethyl acid 3400 (3.4 g, 1 mmol, Shearwater Polymers, Huntsville, Ala.) in toluene was azeotropically distilled for two hours and then cooled to room temperature. A solution of thionyl chloride (2M, 4 ml, 8 mmole, Aldrich) in methylene ride was injected and the mixture was stirred under $N_2$ overnight. The solvent was condensed by rotary evaporation and the syrup was dried in vacuo for about four hours over $P_2O_5$ powder. To the residue was added anhydrous methylene chloride (5 ml) and azeotropically dried benzyloxy-PEG 3400 (2.55 g, 0.75 mmol) in toluene (20 ml). After the benzyloxy-PEG acyl chloride was dissolved, freshly distilled triethylamine (0.6 ml) was added. The mixture was stirred overnight, the triethylamine salt filtered off, and the product collected by precipitation with ethyl ether. It was further purified by dissolving in water and extracting with methylene chloride. The organic phase was dried over anhydrous sodium sulfate, condensed under vacuum, and precipitated into ethyl ether. The precipitate was dried in vacuo. HPLC (GPC) of the product showed that 100% of benzyloxy-PEG had been converted into the PEG ester and about 15 wt. % benzyloxy-PEG acid remained.

The mixture was chromatographically purified on an ion-exchange column (DEAE sepharose fast flow, Pharmacia) to remove the benzyloxy-PEG acid. 100% pure α-benzyloxy-ω-benzyloxy PEG ester 6800 (2 g, 0.59 mmole end group) in 1,4-dioxane (20 ml) was hydrogenolyzed with $H_2$ (2 atm pressure) and Pd/C (1 g, 10% Pd) overnight. The catalyst was removed by filtration and the product precipitated into ethyl after most of the solvent was removed on a rotary evaporator.

α-hydroxy-ω-hydroxy PEG ester 6800 was collected by filtration and dried in vacuo. Yield: 1.5 gram (75%).

α-hydroxy-ω-hydroxy PEG ester 6800 (1.5 g, 0.44 mmole end group) was a zeotropically dried with 100 ml of acetronitrile and cooled to room temperature. To this solution was added disuccimidyl carbonate (DSC) (0.88 mmole, Fluka) and pyridine (0.1 ml), and the solution was stirred at room temperature overnight. The solvent was removed under vacuum and the syrup was dried in vacuo. The product was dissolved in 35 ml of dry methylene chloride, the insoluble solid was removed by filtration, and the filtrate washed with pH 4.5 sodium chloride saturated acetate buffer. The organic phase was dried over anhydrous sodium sulfate, condensed under vacuum, and precipitated into ethyl ether. The precipitate was dried over $P_2O_5$ in vacuo. Yield: 1.4 g (93%). NMR (DMSO-$d_6$): (1) product from benzyloxy-PEG propionic acid: δ3.5 (br m, PEG), 2.55 (t, —OCH$_2$C$\underline{H}_2$COOPEG—), 4.13 (t, —PEG—COOC$\underline{H}_2$CH$_2$O—), 4.45 (t, —PEGOCH$_2$C$\underline{H}_2$OCO—NHS), 2.80b [s, NHS, 4H]; (2) product from benzyloxy-PEG carboxymethyl acid: δ3.5 (br m, PEG), 4.14 (s, —OC$\underline{H}_2$COOPEG—), 4.18 (t, —OCH$_2$COOC$\underline{H}_2$CH$_2$—), 4.45 (t, —PEGO—CH$_2$C$\underline{H}_2$OCONHS), 2.81 [s, NHS, 4H].

Example 2

Synthesis of PEG Derivatives Having Hydrolytically Unstable Backbone Linkages and Terminal NHS Active Esters (NHS—OOC—(CH$_2$)$_n$—O—PEG—O—(CH$_2$)$_n$—CO$_2$—PEG—O$_2$C—(CH$_2$)$_n$—O—PEG—O—(CH$_2$)$_n$—COONHS)

In a 100 ml round-bottom flask, difunctional PEG 2000 (2 g, 1 mmol, Shearwater Polymers) and difunctional PEG acid 2000 (4 g, 2 mmole, Shearwater Polymers) were azeotropically distilled with 70 ml of toluene under $N_2$. After two hours, the solution was cooled to room temperature and stannous 2-ethylhexanoate (200 mg, Sigma Chemical) was added. The solution was then refluxed under $N_2$ for 24 hours. The solvent was then condensed under vacuum and the syrup precipitated into 100 ml of ether. The product was collected by filtration, dried under vacuum, and dissolved in a sodium acetate buffer solution at pH 5.0. The slightly milky solution was centrifuged and the upper clear solution was extracted three times with methylene chloride. The organic phase was dried over anhydrous sodium sulfate, filtered, condensed under vacuum, and precipitated into ether. The product was collected by filtration and dried under vacuum. HPLC: 70% product, 15% di-acid reactant and 15% monoacid. The mixture was further purified by ion exchange chromatography and gel permeation chromatography. Yield 3 g (50%). $^1$H NMR (DMSO-$D_6$): (1) product from PEG carboxymethyl acid: δ6 3.5 (br m, PEG), 4.15 (s, —OC$\underline{H}_2$COOCH$_2$—), 4.18 (t, —OCH$_2$COOC$\underline{H}_2$CH$_2$—), 3.98 (s, —PEG—OC$_{H2}$COOH); (2) product from PEG propionic acid: δ3.5 (br m, PEG), 2.55 (t, —PEGOCH$_2$C$\underline{H}_2$COOCH$_2$—), 4.13 (t, —OCH$_2$CH$_2$COOC$\underline{H}_2$CH$_2$—), 2.43 (t, —PEGOCH$_2$C$\underline{H}_2$COOH)

In a round-bottom, flask, the difunctional acid having weak linkages (obtained from previous step) 3 g. approx. 1 mmole end group) and N-hydroxysuccinimide (NHS) (126 mg, 1.05 mmole) were dissolved in 50 ml of dry methylene chloride. To this solution was added dicyclohexylcarbodiimide.(240 mg, 1.15 mmole) in 5 ml dry methylene chloride. The mixture was stirred under $N_2$ overnight. The solvent was condensed and the syrup was redissolved in 15 ml of anhydrous toluene. The insoluble salt was removed by filtration and the filtrate was precipitated into 200 ml of dry ethyl ether. The precipitate was collected by filtration and dried in vacuo. Yield 2.7 g (90%). $^1$H NMR (DMSO-$d_6$): δ3.5 (br m, PEG), 2.8 (s, NHS, 4H) 4.6 (S, —PEG—O—C$\underline{H}_2$—COONHS) or 2.85 (t, —PEG—O—CH$_2$C$\underline{H}_2$—COONHS).

Example 3

Hydrolysis Kinetics of the Ester Linkages in the Middle of the PEG Derivatives To precisely measure the hydrolysis kinetics of the ester linkages, water-soluble, non-crosslinked mPEG—O—(CH$_2$)$_n$—COO—PEGm was synthesized as in Example 2. Hydrolysis was carried out in buffer solutions (0.1 M) at different pHs and temperatures, and followed by HPLC-GPC (Ultrahydrogel® 250, Waters). The half-lives of the ester bonds are listed in Table 1.

TABLE 1

Hydrolysis half lives (days, ±10%) of the ester of mPEG-O-(CH$_2$)$_n$-COO-PEGm in 0.1 M phosphate buffer.

| pKa of the acid | PA ester linkage 4.45 ± 0.1 | | | CM ester linkage 3.67 ± 0.05 | | |
|---|---|---|---|---|---|---|
| pH | 5.5 | 7.0 | 8.1 | 5.5 | 7.0 | 8.1 |
| Room Temp. (22–23° C.) | >500 | 250 | 37 | >150 | 30 | 5 |
| 37° C. | | 43 | | | 4 | |
| 50° C. | | 15 | | | 1.5 | |

Example 4

Preparation of a Hydrolytically Unstable PEG Hydrogel from Branched PEG Amine, Model Protein (FITC-ESA) and PEG Derivatives Having Hydrolytically-unstable Backbone Linkages and Terminal NHS Active Carbonates (NHS—OOCO—PEG—W—PEG—OCOONHS)

In a test tube, i6o mg (14.7 μmole) of difunctional PEG active carbonate 6800 (NHS—OOCO—PEG—W—PEG—OCOONHS, prepared in Example 1) was dissolved in 0.75 ml of buffer (0.1M phosphate, pH 7). To the solution were added 0.15 ml of 8-arm-PEG-amine boon (250 mg/ml) and 0.1 ml of FITC-BSA (10 mg/ml). After rapid shaking, it was allowed to sit and a gel formed in a few minutes. A suitable buffer pH range was found to be 5.5 to 8.

Example 5

Preparation of a Hydrolytically Unstable PEG Hydrogel from Branched PEG Amine, Model Protein, and PEG Derivatives Having Hydrolytically Unstable Backbone Linkages and Terminal NHS Active Esters (NHS—OOC—$(CH_2)_n$—O—PEG—O—$(CH_2)_n$—$CO_2$—PEG—$O_2C$—$(CH_2)_n$—O—PEG—O—$(CH_2)_n$—COONHS)

100 mg (approx. 16.6 μmole) difunctional PEG active ester (NHS—OOC—$(CH_2)_n$—O—PEG—O—$(CH_2)_n$—$CO_2$—PEG—$O_2C$—$(CH_2)_n$—O—PEG—O—$(CH_2)_n$—COONHS, prepared in Example 2) was dissolved in 0.75 ml of buffer (0.1M phosphate, pH 7). To the solution were added 0.166 ml of 8-arm-PEG-amine 10000 (250 mg/ml) and 0.1 ml of FITC-BSA (10 mg/ml). After rapid shaking, it was₁ allowed to sit and a gel formed in a few minutes. A suitable buffer pH range was found to be 5.5 to 8.

Example 6

Studies of Release of Model Proteins from Hydrolytically Degradable Hydrogels

All protein-loaded hydrogel disks were weighed and their diameters: measured before release studies. Then each gel disk was immersed, at time t=0, in phosphate buffer (0.1 M,pH 7.0). The amount of the buffer was more than 50 times that of the wet gel weight. The solution was maintained at 37° C., and gently shaken. At a predetermined time, a small amount of buffer solution was removed for protein concentration determination and then put back after measurement. The protein concentration was determined by UV measurement at 495 nm. FIG. 1 shows some release profiles of PEG-FITC-BSA from the hydrogels in units plotted against time in days of the fraction of moles at time t divided by the moles at infinity, which is defined as the completion of degradation of the hydrogel.

The invention has been described in particular exemplified embodiments. However, the foregoing description is not intended to limit the invention to the exemplified embodiments, and the skilled artisan should recognize that variations can be made within the scope of the invention as described in the foregoing specification. The invention includes all alternatives, modifications, and equivalents that may be included within the true spirit and scope of the invention as defined by the appended claims.

That which is claimed is:

1. A method of preparing a crosslinked polymeric structure that hydrolyzes to release at least one conjugate of a biologically active molecule with a substantially non-peptidic polymer, comprising reacting (1) a PEG molecule having at least one hydrolytically unstable linkage in its backbone, (2) a branched, substantially non-peptidic polymeric amine, and (3) a biologically active molecule to form the polymeric structure, wherein the hydrolytically unstable linkage is capable of degrading to release a conjugate of the biologically active molecule and a substantially non-peptidic polymer.

2. The method of claim 1 wherein the reaction can be represented by the following:

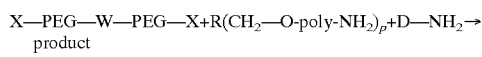

$$X\text{—PEG—W—PEG—}X + R(CH_2\text{—O-poly-}NH_2)_p + D\text{—}NH_2 \rightarrow \text{product}$$

wherein

X is selected from the group consisting of succinimidyl ester, sulfosuccinimidyl, benzotriazole, and p-nitrophenyl;

R is a central branching group leading to branched polymers poly that is selected from the group consisting of glycerol, glycerol oligomers, pentaerythritol, sorbitol, trimethyolpropane, and di(trimethylolpropane);

p=3 to 10 and represents to the degree of branching of the branched polymer poly;

poly is a polymer selected from the group consisting of poly(alkylene oxides), poly(oxyethylated polyols), poly(olefininc alcohols), arid poly(acrylomorpholine);

W is a hydrolytically unstable linkage selected from the group consisting of carboxylate ester, phosphate ester, orthoester, anhydride, imine, acetal, ketal, oligonucleotide, and peptide; and D is a biologically active molecule.

3. The method of claim 2 wherein X is —O—$(CH_2)_n$—$CO_2$—NHS or —O—$CO_2$NHS, and wherein n=1–10.

4. The method of claim 2 wherein W is an ester linkage O—$(CHR')_r$—$CO_2$—, wherein r=1 through 10, and R' is hydrogen or alkyl.

5. The method of claim 1 wherein the branched, substantially non-peptidic polymeric amine does not have hydrolytically unstable linkages in its backbone.

6. The method of claim 2 wherein poly is selected from the group consisting of poly(alkylene oxides), poly(vinyl pyrrolidone), poly(vinyl alcohol), polyoxazoline, and poly(acryiloylmorpholine).

7. The method of claim 1 wherein the branched, substantially non-peptidic polymeric amine is selected from the group consisting of poly(alkylene oxides), poly(oxyethylated polyols), poly(olefininc alcohols), and poly(acrylomorpholine).

8. The method of claim 1 wherein the branched, substantially non-peptidic polymeric amine is poly(ethylene glycol).

9. The method of claim 1 wherein the at least one hydrolytically unstable linkage is selected from the group consisting of carboxylate ester, phosphate ester, orthoester, anhydride, imine, acetal, ketal, oligonucleotide, and peptide.

10. The method of claim 1 wherein the branched, substantially non-peptidic polymeric amine has the structure $R(CH_2\text{—O-poly-}NH_2)_p$, wherein R is a central branching group, p is 3 to 10, and poly is a polymer selected from the group consisting of poly(alkylene oxides), poly(oxyethylated polyols), poly(olefininc alcohols), and poly(acrylomorpholine).

11. The method of claim 10 wherein poly is poly(ethylene glycol).

12. The method of claim 10 wherein R is selected from the group consisting of glycerol, glycerol oligomers, pentaerythritol, sorbitol, trimethyolpropane, and di(trimethylolpropane).

13. The method of claim 1 wherein the biologically active molecule is selected from the group consisting of enzymes, polypeptides, drugs, nucleosides, and phospholipids.

14. The method of claim 1 wherein the biologically active molecule comprises at least one amine group.

15. The method of claim 1 wherein said reacting step results in a hydrolytically stable linkage between the biologically active molecule and the PEG molecule having at least one hydrolytically unstable linkage in its backbone.

16. The method of claim 15 wherein the hydrolytically stable linkage is selected from the group consisting of amide, urethane, amine, ether, thioether, and urea.

17. The method of claim 1 wherein the PEG molecule is formed by reacting two PEG molecules having different terminal groups, the reaction represented by the following:

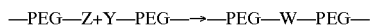

—PEG—Z+Y—PEG—→—PEG—W—PEG— wherein W is a hydrolytically unstable linkage and Z and Y are terminal functional groups capable of reacting to form W.

18. The method of claim 17 wherein Z is an alcohol, Y is a carboxylic acid, and W is a carboxylate ester.

19. The method of claim 17 wherein Z is an amine, Y is an aldehyde, and W is an imine.

20. The method of claim 17 wherein Z is a hydrazide, Y is an aldehyde, and W is a hydrozone.

21. The method of claim 17 wherein Z is an alcohol, Y is a phosphate, and W is a phosphate ester.

22. The method of claim 17 wherein Z is an alcohol, Y is an aldehyde, and W is an acetal.

23. The method of claim 17 wherein Z is an alcohol, Y is a formate, and W is an orthoester.

24. The method of claim 1 wherein the PEG molecule has at least two hydrolytically unstable linkages in its backbone.

25. The method of claim 24 wherein the PEG molecule has the formula: NHS—O$_2$C—CH$_2$—O—PEG—O—CH$_2$—CO$_2$—PEG—O$_2$C—CH$_2$—O—PEG—O—CH$_2$—CO$_2$—NHS, wherein NHS is succinimidyl.

26. The method of claim 6 wherein the PEG molecule has the formula X—PEG—W—PEG—X, wherein each X is a terminal reactive group and W is a hydrolytically unstable linkage.

27. The method of claim 26 wherein each X is independently selected from the group consisting of succinimidyl ester, sulfosuccinimidyl, benzotriazole, and p-nitrophenyl.

28. The method of claim 27 wherein X is —O—(CH$_2$)$_n$—CO$_2$—NHS or —O—CO$_2$NHS, wherein n 1–10.

29. The method of claim 26 wherein W is selected from the group consisting of carboxylate ester, phosphate ester, orthoester, anhydride, imine, acetal, ketal, oligonucleotide, and peptide.

30. The method of claim 26 wherein W is —O—(CHR')$_r$—CO$_2$—, wherein r 1 through 10, and R' is hydrogen or alkyl.

31. The method of claim 1 wherein the PEG molecule has the structure NHS—OOC—(CH$_2$)$_n$—O—PEG—O—(CH$_2$)$_n$—CO$_2$—PEG—O$_2$C—(CH$_2$)$_n$—O—PEG—O—(CH$_2$)$_n$—COONHS, wherein each n is independently 1–10.

32. The method of claim 1 wherein the hydrolytically unstable linkage is an ester linkage —O(CHR')$_r$—CO$_2$—, wherein r=1 through 10, and R' is hydrogen or alkyl.

33. A method of preparing a crosslinked polymeric structure that hydrolyzes to release at least one conjugate of a biologically active molecule with a poly(ethylene glycol) polymer molecule, comprising reacting (1) a PEG molecule having at least one hydrolytically unstable linkage in its backbone, (2) a branched PEG amine, and (3) a biologically active molecule to form the polymeric structure, wherein a hydrolytically stable linkage is formed between the hydrolytically unstable PEG molecule and the biologically active molecule, and wherein the hydrolytically unstable linkage in the backbone of the PEG molecule is capable of degrading to release a conjugate of the biologically active molecule and poly(ethylene glycol).

34. The method of claim 33 wherein the hydrolytically unstable linkage is selected from the group Consisting of carboxylate ester, phosphate ester, orthoester, anhydride, imine, acetal, ketal, oligonucleotide, and peptide.

35. The method of claim 33 wherein the hydrolytically unstable linkage is an ester linkage —O—(CHR')$_r$—CO$_2$—, wherein r=1 through 10, and R' is hydrogen or alkyl.

36. The method of claim 33 wherein the hydrolytically stable linkage is selected from the group consisting of amide, urethane, amine, ether, thioether, and urea.

37. The method of claim 33 wherein the PEG molecule is formed by reacting two PEG molecules having different terminal groups, the reaction represented by the following:

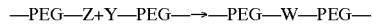

—PEG—Z+Y—PEG—→—PEG—W—PEG— wherein W is a hydrolytically unstable linkage and Z and Y are terminal functional groups capable of reacting to form W.

38. The method of claim 33 wherein the PEG molecule has the formula X—PEG—W—PEG—X, wherein each X is a terminal reactive group and W is a hydrolytically unstable linkage.

39. The method of claim 38 wherein each X is independently selected from the group consisting of succinimidyl ester, sulfosuccinimidyl, benzotriazole, and p-nitrophenyl.

40. The method of claim 33 wherein the PEG molecule has at least two hydrolytically unstable linkages in its backbone.

* * * * *

UNITED STATES PATENT AND TRADEMARK OFFICE
CERTIFICATE OF CORRECTION

PATENT NO. : 6,432,397 B1  
DATED : August 13, 2002  
INVENTOR(S) : Harris

It is certified that error appears in the above-identified patent and that said Letters Patent is hereby corrected as shown below:

Column 10,
Line 46, "(acryiloylmorpholine)" should read -- (acryloylmorpholine) --.

Column 11,
Line 44, "claim 6" should read -- claim 1 --;
Line 52, "n 1-10" should read -- n=1-10 --.

Column 12,
Line 2, "r 1 through 10" should read -- r = 1 through 10 --;
Line 25, "Consisting" should read -- consisting --.

Signed and Sealed this

Seventh Day of January, 2003

JAMES E. ROGAN
*Director of the United States Patent and Trademark Office*